(12) United States Patent
Snyder et al.

(10) Patent No.: US 9,316,545 B2
(45) Date of Patent: *Apr. 19, 2016

(54) SCANNING MEASUREMENT OF SEEBECK COEFFICIENT OF A HEATED SAMPLE

(75) Inventors: G. Jeffrey Snyder, Pasadena, CA (US); Shiho Iwanaga, Rancho Palos Verdes, CA (US)

(73) Assignee: California Institute of Technology, Pasadena, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 13/547,006

(22) Filed: Jul. 11, 2012

(65) Prior Publication Data

US 2013/0044788 A1 Feb. 21, 2013

Related U.S. Application Data

(63) Continuation-in-part of application No. 13/403,835, filed on Feb. 23, 2012.

(60) Provisional application No. 61/506,499, filed on Jul. 11, 2011.

(51) Int. Cl.
*G01K 7/00* (2006.01)
*G01K 7/02* (2006.01)
*G01N 25/72* (2006.01)

(52) U.S. Cl.
CPC . *G01K 7/02* (2013.01); *G01N 25/72* (2013.01)

(58) Field of Classification Search
CPC .................................................. G01K 7/02
USPC .......................................... 374/179, E07.004
See application file for complete search history.

(56) References Cited

U.S. PATENT DOCUMENTS

| | | | | |
|---|---|---|---|---|
| 6,459,069 | B1* | 10/2002 | Rabinovich | 219/121.63 |
| 6,467,951 | B1* | 10/2002 | Ghoshal | 374/45 |
| 7,175,343 | B2* | 2/2007 | Phillips | 374/180 |
| 2005/0023269 | A1* | 2/2005 | Hiramatsu et al. | 219/444.1 |
| 2005/0035773 | A1* | 2/2005 | Wang et al. | 324/715 |
| 2007/0250275 | A1* | 10/2007 | Ohashi et al. | 702/33 |

FOREIGN PATENT DOCUMENTS

JP 2009258032 A * 11/2009

OTHER PUBLICATIONS

D. Platzek, A. Zuber, C. Stiewe G. Bahr, P. Reinshaus and E. Miille', An Automated Microprobe for Temperature Dependent Spatial Scanning of the Seebeck Coefficient, pp. 528-531, 22'" InIcmalional Confcrcncc on 'Ihcrmoclcclrics (2003).*

(Continued)

Primary Examiner — Lisa Caputo
Assistant Examiner — Nasir U Ahmed
(74) Attorney, Agent, or Firm — Canady & Lortz LLP; Bradley K. Lortz (57) ABSTRACT

A novel scanning Seebeck coefficient measurement technique is disclosed utilizing a cold scanning thermocouple probe tip on heated bulk and thin film samples. The system measures variations in the Seebeck coefficient within the samples. The apparatus may be used for two dimensional mapping of the Seebeck coefficient on the bulk and thin film samples. This technique can be utilized for detection of defective regions, as well as phase separations in the sub-mm range of various thermoelectric materials.

21 Claims, 10 Drawing Sheets (56) References Cited

OTHER PUBLICATIONS

Wood et al., "Measurement of Seebeck coefficient using a light pulse," Rev. Sci. Instrum. 56 (5), May 1985, pp. 719-22.
Martin et al., "High Temperature Seebeck coefficient metrology," Journal of Applied Physics 108, 121101, Dec. 2010.
Wood et al., "Measurement of Seebeck coefficient using large thermal gradient," Rev. Sci. Instrum. 59 (6), Jun. 1988, pp. 951-54.
Platzek et al., "Potential-Seebeck-Microprobe (PSM): Measuring the Spatial . . . ," 0-7803-9552-2, IEEE, International Conf. on Thermoelectrics, 2005.

* cited by examiner

SCANNING MEASUREMENT OF SEEBECK COEFFICIENT OF A HEATED SAMPLE

CROSS-REFERENCE TO RELATED APPLICATIONS

This application claims the benefit under 35 U.S.C. §119 (e) of the following U.S. provisional patent application, which is incorporated by reference herein:

U.S. Provisional Patent Application No. 61/506,499, filed Jul. 11, 2011, and entitled "Scanning Method for Measurement of Seebeck Coefficient on Bulk and Thin Film Materials", by Snyder.

This application is a Continuation-In-Part of the following co-pending and commonly-assigned U.S. utility patent application, which is incorporated by reference herein:

U.S. patent application Ser. No. 13/403,835, filed Feb. 23, 2012, and entitled "Measuring Seebeck Coefficient", by Snyder et al..

STATEMENT OF GOVERNMENT RIGHTS

This invention was made with government support under DE-AR0000033 awarded by the Department of Energy. The government has certain rights in the invention.

BACKGROUND OF THE INVENTION

1. Field of the Invention

This invention relates to determining the Seebeck coefficient for thermoelectric materials. Particularly, this invention relates to scanning measurement of the Seebeck coefficient of thermoelectric materials to reveal local variations and inhomogeneities.

2. Description of the Related Art

An applied temperature difference across a material causes charged carriers in the material (electrons or holes) to diffuse from the hot side to the cold side. Mobile charged carriers migrating from the hot to the cold side leave behind their oppositely charged and immobile nuclei, resulting in a thermoelectric voltage across the material. The term, "thermoelectric," refers to the fact that the voltage is created by a temperature difference. Since a separation of charges also yields an electric field, the buildup of charged carriers on the cold side eventually ceases at some maximum value for a given temperature difference as there exists an equal amount of charged carriers drifting back to the hot side as a result of the electric field equilibrium. An increase in the temperature difference can result in more charge carriers on the cold side and thus yield an increase in the thermoelectric voltage.

The Seebeck coefficient (or thermopower) is a measure of the magnitude of an induced thermoelectric voltage in response to a temperature difference across a given material. The Seebeck coefficient has units of volts per degrees kelvin.

$$S = \frac{\Delta V}{\Delta T} \quad (1)$$

The Seebeck coefficient, S, depends on a material's temperature, and crystal structure. Typically, metals have small thermopowers because most have half-filled bands, including both electrons and holes. Electrons (negative charges) and holes (positive charges) both contribute to the induced thermoelectric voltage thus tending cancel their contributions to that voltage, resulting in a low net voltage. In contrast, semiconductors can be doped with an excess amount of electrons or holes and therefore can have large positive or negative values of the thermopower depending on the charge of the excess carriers. The sign of the thermopower indicates which charged carriers dominate the electric transport in both metals and semiconductors.

Accurate measurement of the Seebeck coefficient is critical for the performance assessment of thermoelectric materials. The history and challenges of Seebeck coefficient measurement has been recently reviewed. See e.g. J. Martin, T. Tritt, and C. Uher, J. Appl. Phys. 108, 121101 (2010), which is incorporated by reference herein.

The process development for large scale, homogeneous thermoelectric materials has become increasingly important due to expanding thermoelectric device product demands in various markets including the automobile industry and Peltier cooling. Recently, a number of stable materials with relatively high ZT (~1.5), such as sodium doped PbTe, have been developed. In order to bring new types of thermoelectric materials into commercial products, the scale-up of fabrication technology is necessary.

Typical bulk prototype materials are small sized samples with sizes of about 10 mm×10 mm×1 mm. A fabricated device generally contains a large number of thermoelectric material pieces, shaped into columns by cutting a large bulk material piece. Materials fabrication techniques including the Bridgman method, Czochralski, zone-melting, variations of hot-press and Spark Plasma Sintering are often utilized to fabricate a large bulk During these processes, unintentional phase separations, grain orientation misalignments, and vacancy sites can be introduced anywhere in the bulk. This often creates local variations in a material composition thus variations in the thermoelectric parameters. For the mass production of devices, this should be avoided because each piece will have different properties, depending on where the piece was cut out from. Therefore, monitoring homogeneity of the material becomes an important part of the process optimization technique. This can be realized by detecting spatial variations of the Seebeck coefficient using apparatus such as a scanning Seebeck coefficient measurement system. This type of system has been explored and developed into production by companies such as Ulvac-Riko Inc. and PANCO GmbH. A typical setup employs a heated scanning probe ('hot probe') to create the temperature gradient within a sample that is necessary for the measurement.

For example, Platzek et al., "Potential-Seebeck-Microprobe (PSM): Measuring the Spatial Resolution of the Seebeck Coefficient and the Electric Potential," 2005 International Conference on Thermoelectrics, which is incorporated by reference herein, discloses a scanning Seebeck Microprobe has been combined with the measurement of the electric potential along the surface of semiconducting or metallic material. A heated probe tip is placed onto the surface of the sample under investigation, measuring the Seebeck coefficient. Using a specially designed sample holder, an AC current can be applied to the specimen, allowing for the detection of the voltage drop between one current contact and the travelling probe tip. This voltage is proportional to the electrical conductivity at the tip position. With this technique a spatially resolved imaging of the Seebeck coefficient as well as the electrical conductivity can be performed. Furthermore the electrical contact resistance between different materials becomes visible, e.g., in segmented thermoelectric or other devices.

In view of the foregoing, there is a need in the art for improved apparatuses and methods for accurately measuring the Seebeck coefficient of thermoelectric materials. There is particularly a need for such apparatuses and methods to detect inhomogeneity in material compositions and defects throughout the thermoelectric materials. Further, there is a need for such apparatuses and methods to be simple, non-destructive, efficient, fast and affordable. There is also a need for such systems and methods to be suitable for thin film material samples. These and other needs are met by embodiments of the present invention as detailed hereafter.

SUMMARY OF THE INVENTION

A novel scanning Seebeck coefficient measurement technique is disclosed utilizing a cold scanning thermocouple probe tip on heated bulk and thin film samples. The system measures variations in the Seebeck coefficient within the samples. The apparatus may be used for two dimensional mapping of the Seebeck coefficient on the bulk and thin film samples. This technique can be utilized for detection of defective regions, as well as phase separations in the sub-mm range of various thermoelectric materials.

A typical embodiment of the invention comprises an apparatus for measuring a Seebeck coefficient of a sample, comprising a mount stage for the sample, the mount stage having a heater for heating a back surface of the sample, a first thermocouple probe having a first contact point where temperature and voltage are measured, a second thermocouple probe having a second contact point where temperature and voltage are measured, the second contact point disposed at a fixed point against the sample distal from the first contact point, and a motorized stage supporting the first thermocouple probe for positioning the first contact point of the first thermocouple probe at different locations on a front surface of the sample. Contact between the first thermocouple probe and the sample creates a local cold spot at the first contact point on the sample and the Seebeck coefficient of the sample proximate to the first contact point is determined from the temperature and voltage measured substantially simultaneously from the first thermocouple probe and the temperature and voltage measured from the second thermocouple probe for each of the different locations on the front surface of the sample. The sample may be a bulk sample where the second contact point is disposed on the back surface of the sample heated by the heater or a thin film sample where the second contact point is disposed on the front surface of the sample near an edge of the sample. Typically, the heater is operated to maintain the sample at a substantially steady state temperature.

In some embodiments, the first thermocouple probe may be spring loaded against the front surface of the sample at the first contact point to allow smooth consistent contact as the first thermocouple probe positioned to the different locations on the front surface of the sample. In further embodiments, a Seebeck coefficient image of the sample is generated from the Seebeck coefficient for each of the different locations on the front surface of the sample.

In some embodiments, the first thermocouple probe comprises an electrically insulating cylinder having four bores exiting at an end surface of the cylinder and two thin wires, each wire threaded through two of the four bores and crossing to contact each other at the end surface. The two thin wires may comprise material combinations X/Y of niobium/chromel, niobium/tungsten, niobium/tungsten-rhenium, copper/constantan, or gold-iron/chromel, where X is a first wire material disposed on top of a second wire material Y. In addition, the electrically insulating cylinder may comprise a ceramic, such as alumina.

A typical method embodiment of measuring a Seebeck coefficient of a sample, comprises heating a back surface of the sample with a heater on a mount stage, the mount stage supporting the sample, measuring temperature and voltage at a first contact point of a first thermocouple probe such that contact between the first thermocouple probe and the sample creates a local cold spot at the first contact point on the sample, measuring temperature and voltage at a second contact point of a second thermocouple probe substantially simultaneously with measuring of the first thermocouple probe, the second contact point disposed at a fixed point against the sample distal from the first contact point, positioning the first contact point of the first thermocouple probe at different locations on a front surface of the sample with a motorized stage supporting the first thermocouple probe, and determining the Seebeck coefficient of the sample proximate to the first contact point from the temperature and voltage measured substantially simultaneously from the first thermocouple probe and the temperature and voltage measured from the second thermocouple probe for each of the different locations on the front surface of the sample. This method embodiment of the invention may be further modified consistent with the apparatus embodiments described herein.

Another typical embodiment of the invention may comprise an apparatus for measuring a Seebeck coefficient of a sample, including a mount stage means for supporting the sample heating a back surface of the sample, a first thermocouple probe means for sensing temperature and voltage at a first contact point, a second thermocouple probe means for sensing temperature and voltage at a second contact point, the second contact point disposed at a fixed point against the sample distal from the first contact point, and a motorized stage means for supporting the first thermocouple probe means and for positioning the first contact point of the first thermocouple probe means at different locations on a front surface of the sample. Contact between the first thermocouple probe means and the sample creates a local cold spot at the first contact point on the sample and the Seebeck coefficient of the sample proximate to the first contact point is determined from the temperature and voltage sensed substantially simultaneously from the first thermocouple probe means and the temperature and voltage sensed from the second thermocouple probe means for each of the different locations on the front surface of the sample. This embodiment of the invention may be further modified consistent with the apparatus or method embodiments described herein.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

As previously discussed, the scale-up of the thermoelectric materials fabrication techniques is necessary for the mass production of thermoelectric devices at an industrial level. Some fabrication techniques can create inhomogeneity in material compositions or defects throughout the thermoelectric materials, causing local variations in the thermoelectric properties. Some variations are in the range of sub-mm scale or larger, but may be difficult to be detected by traditional materials characterization techniques such as X-ray diffraction and the scanning electron microscopy when the chemical variation is small but the doping variation, which greatly determines thermoelectric performance, is large.

Embodiments of the present invention employ a simple scanning Seebeck coefficient system and method utilizing a 'cold probe' technique. A significant feature of the instrument is that, the heater may be located on the sample holder side and the cold scanning probe creates a local cold spot on a sample to generate the temperature gradient needed for the Seebeck coefficient measurement. Two dimensional mapping of the Seebeck coefficient may demonstrated on both bulk and thin film samples. This cold probe technique is beneficial especially for thin film samples, since it does not require any sample preparation prior to the measurements: the deposited films can be measured as is. Further, the instrument delivers significantly small standard deviation of the Seebeck coefficient measurement, which is less than 1 µV/K. With such high measurement stability and low noise level, this apparatus can be utilized not only for quality control of mass-produce materials but also for other purposes such as evaluation of the Seebeck coefficient for combinatorial materials researches and other functionally graded materials. An example scanning Seebeck coefficient measurement system may be employed to yield images for both bulk and thin film samples and absolute Seebeck coefficient evaluation on compositionally gradient material. In addition, the system exhibits low level noise of allowed the Seebeck coefficient on compositionally graded materials, which only has slight variations in the Seebeck coefficient.

2. Measuring Seebeck Coefficient

Figure 1:
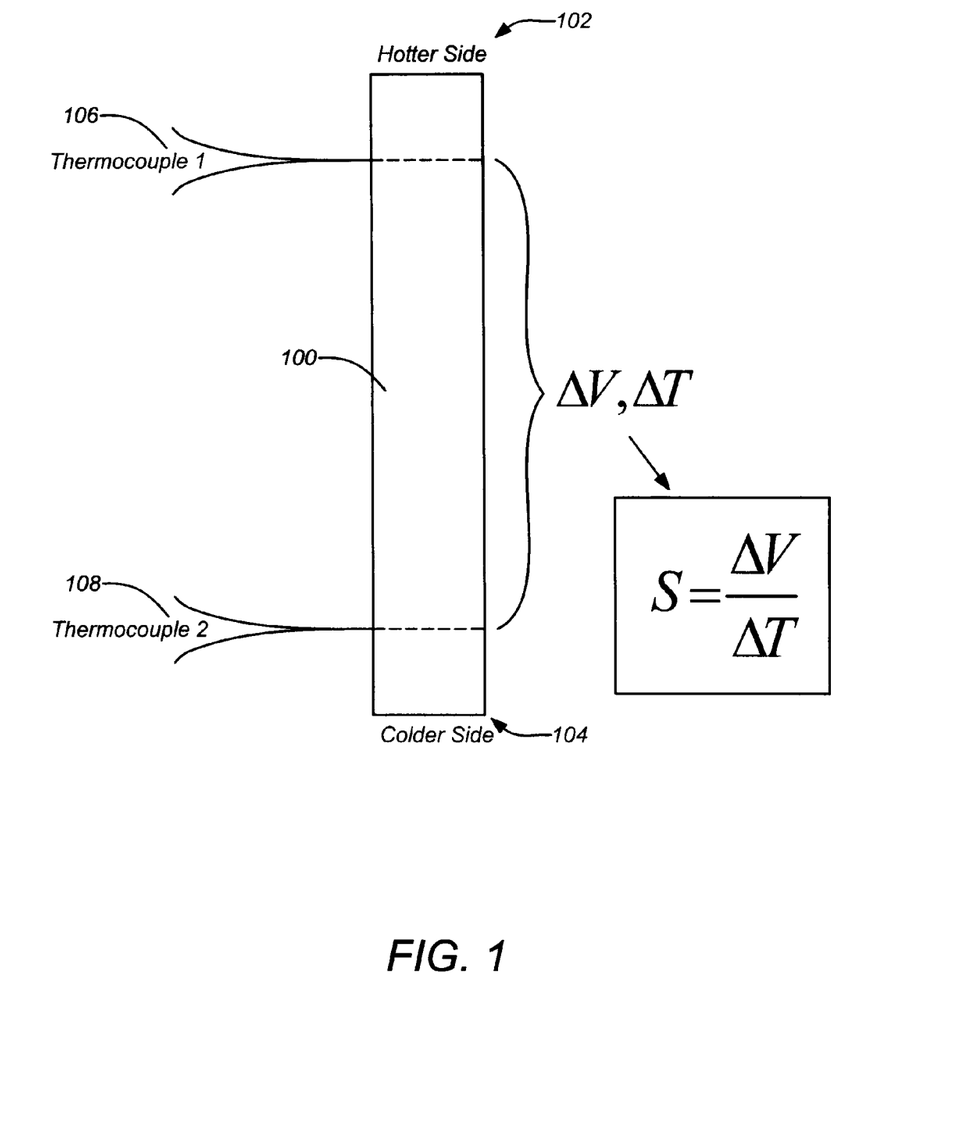
FIG. 1 is a schematic diagram of ideal measurement geometry for the Seebeck coefficient, with thermocouples making small point contacts.

FIG. 1 shows idealized measurement geometry for the Seebeck coefficient where two probes 106, 108 make point contacts with the sample material 100 at precise locations across a temperature gradient between a hot side 102 and a cold side 104 of the sample material 100. In principle, measurement of the Seebeck coefficient in bulk materials is relatively simple. One needs to know the temperature gradient between two locations on a sample, and the voltage across the two points. The probes 106, 108 serve as both the thermocouples as well as the voltage measurement leads, across which the temperature gradient and voltage present are measured. (It should be noted that for every example measurement system described herein, thermocouples also serve as the voltage measurement leads unless otherwise stated.) For an ideal measurement of the Seebeck coefficient, certain assumptions are applied. First, the system is assumed to be in steady state during the measurement of the temperature and voltage, and that both measurements occur simultaneously. In addition, it is also assumed that the voltage response to the temperature gradient is linear and that the measurement of the temperature and voltage occur at the same point on the sample for each probe.

It should be noted that throughout this description a temperature gradient across a material may be established by two elements, one having a hotter temperature than the other. These elements may be described as either a heater or a cooler depending upon their temperatures relative to the ambient tempurature. However, the term, "heater," will be used generically thoughout this description to mean both the hotter and the colder element used in a system. Measurement of the Seebeck coefficient only concerns their temperatures relative to each other; their temperatures relative to the ambient temperature is not a factor.

However, in a real instrument, non-negligible errors often result due to the inability to achieve these ideal conditions. For example, temperature and voltage measurements often occur at different times in practice. In addition, the voltage response to the temperature gradient is often not linear in practice due to insufficient signal or non-zero voltage at $\Delta T=0$. Furthermore, during high temperature measurements, there is often a noticeable voltage offset that results in significant inaccuracies arising from simple $\Delta V/\Delta T$ measurement. The origin of this voltage offset may be unclear, but it has been found to increase with temperature and can become particularly significant at temperatures greater than 300 C. Finally, true co-location of the measurement of the temperature and voltage is almost never attained, as there is always some distance between the temperature and voltage measurement locations due to the finite size of the temperature sensor. The smallest point source temperature sensor used in Seebeck measurement is a thermocouple probe. However, in a thermocouple junction, the temperature where the wires meet is not necessarily the same as the sample temperature associated with the voltage measurement.

Having identified some sources of Seebeck coefficient measurement error, embodiments of the present invention can minimize these effects in order to obtain more accurate measurements of the Seebeck coefficient. Particularly, a novel thermocouple probe design may be employed with embodiments of the invention as described in section 4 hereafter.

3. Scanning Seebeck Coefficient Apparatuses

The Seebeck coefficient indicates the amount of voltage ($\Delta V$) that develops from a given temperature difference ($\Delta T$) in a material, which can be given from the equation $S=\Delta V/\Delta T$. Experimentally, a single data point of the Seebeck coefficient can be achieved by measuring the temperature of the two locations on a sample, and the voltage across these locations, measured substantially simultaneously. The temperature gradient in a sample can be provided by an external heat source proximate to one side of the sample.

In a typical scanning system, a first probe with a thermocouple junction at the tip is employed that makes a direct contact with the sample front surface. A second thermocouple junction may securely fixed onto a sample mount stage with the junction making a direct contact (or placed nearby) the back surface of the sample surface. The motorized stage or the first probe allows relative movement in the x and y direction over the front surface of the sample. Optionally, z direction motion for the first probe contact can also be realized by the programmed motor motion.

Figure 2A:
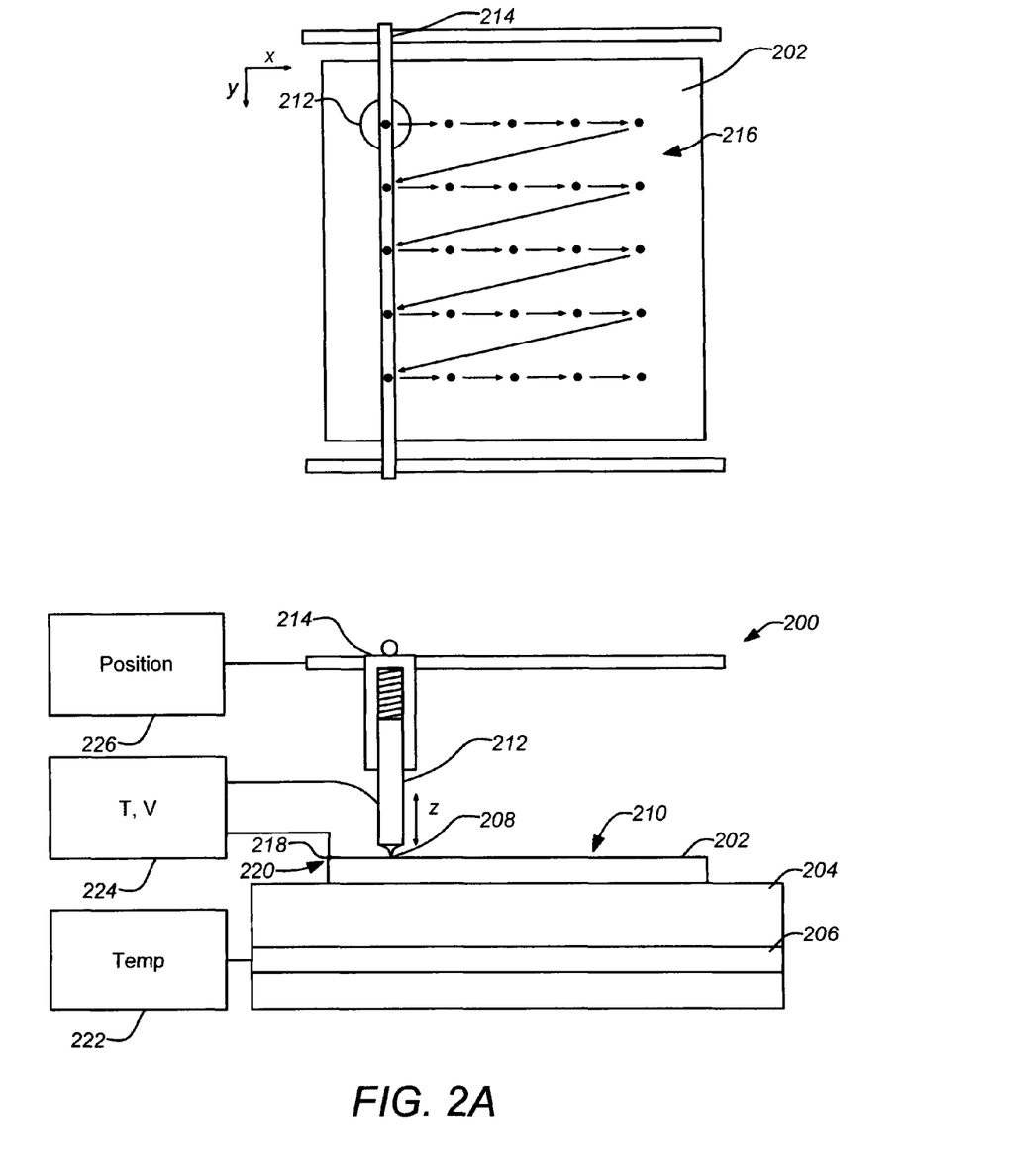
FIG. 2A is a schematic diagram of an exemplary apparatus for scanning measurement of the Seebeck coefficient at a local contact point of a sample.

FIG. 2A is a schematic diagram of an exemplary apparatus 200 for scanning measurement of the Seebeck coefficient at a local contact point of a sample 202. The lower image shows a side view of the apparatus 200 and the upper image shows a top view of an example scanning sequence over the sample 200. The sample 202 is supported by a mount stage 204 having a heater 206 for heating the back surface of the sample 202. The heater 206 may be disposed on the top surface of the mount stage 204 or within it such that heat is delivered to the sample through conduction.

The first thermocouple probe 212 contact point 208 at the scanning tip, which is at room temperature, makes contact with the front surface 210 of the sample 202 from above. In general, when a thermocouple probe 212 with a large thermal mass (relative to the sample) makes contact with a material, the thermal conductance of the thermocouple probe 212 draws heat away from the material (known as 'cold finger effect') resulting in a local cold spot of the material proximate to the tip of the thermocouple probe 212. Accordingly, embodiments of the invention employ a first thermocouple probe 212 of sufficient thermal mass relative to the sample 202 to create a local cold spot at the first contact point 208 on the sample 202. The scanning thermocouple probe may comprise a four-bore alumina (or alternately, mullite) insulating tube, for example, and its thermal mass creates a local cold spot on the sample surface when contacting it. The first contact point of the first thermocouple probe is where temperature and voltage are measured. Details of suitable first thermocouple probe 212 design are provided in the following section. A second thermocouple probe 218 is disposed at a fixed point against the sample 202 distal from the first contact point 208. The second thermocouple probe 218 has a second contact point 220 where temperature and voltage are measured. Placement of the second thermocouple probe 218 may vary depending upon whether a bulk or thin film sample is being tested as described hereafter.

A motorized stage 214 supports the first thermocouple probe 212 for positioning the first contact point 208 of the first thermocouple probe 212 at different locations 216 on the front surface 210 of the sample 202. The Seebeck coefficient of the sample proximate to the first contact point 208 is determined from the temperature and voltage measured substantially simultaneously from both the first thermocouple probe and the second thermocouple probe for each of the different locations 216 on the front surface 210 of the sample 202. The motorized stage 214 positions the thermocouple probe 212 between each measurement. Any suitable motorized stage 214 may be used in embodiments of the invention. The motorized stage 214 must control motion in at least two dimensions (the x-y plane of the front surface 210 of the sample 202). In the two dimensional motion case, the thermocouple probe 212 is spring loaded against the front surface 210 of the sample 202. Optionally, the motorized stage 214 may control motion in three dimensions such that the thermocouple probe 212 is made to contact the front surface 210 of the sample 202 and lifted off (in the z direction) as the probe 212 is moved between each measurement position.

A Seebeck coefficient image and histogram may be derived from the various measurements from the different locations 216. Distances along the sample surface 210 between each measurement are determined by the desired image resolution. The measurements may be taken in any suitable order. For example, the upper image of FIG. 2A shows a pattern where each line of horizontal measurements along the x axis are performed in sequence along the y axis. Alternately, the measurements may be performed in a meanderline pattern with each successive line of measurements performed in the opposite direction of the preceding line. Image data must be appropriately compiled in this case.

Function of the measurement apparatus 200 may be performed through coordinated operation of various control units. A temperature control unit 222 may be used to control the temperature of the sample 202. Typically, the temperature control unit 222 will hold the temperature at a predetermined steady state temperature. A measurement unit 224 may be used to take the substantially simultaneous temperature and voltage measurements from the thermocouple probes 212, 218. The motorized stage control unit 226 may be used to position the first thermocouple probe 212 between measurements. The control units may be separate units or combined in a single unit. Typically, the measurement apparatus 200 may be implemented through computer controlled operation. Particularly, compiling of the measurement data is best facilitated through a computer. The measurement apparatus 200 may be alternately configured for bulk or thin film sample testing.

Figure 2B:
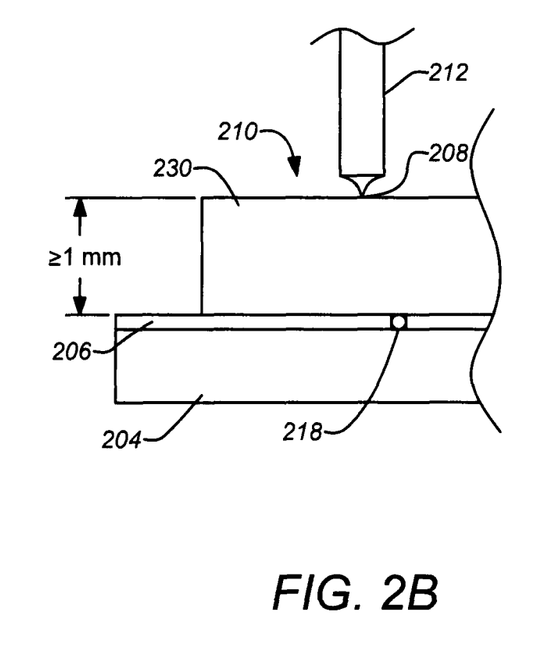
FIG. 2B is a schematic diagram of the exemplary apparatus for scanning measurement of the Seebeck coefficient at a local contact point of a sample for a bulk sample.

FIG. 2B is a close-up schematic diagram of the exemplary apparatus for scanning measurement of the Seebeck coefficient at a local contact point of a sample for a bulk sample. A typical bulk sample 230 may have a thickness of at least 1 mm. For the bulk sample measurement, the second thermocouple may be located on the mount stage 204 (e.g. on the heater 206), making contact with the back surface facing the heater or the sidewall of the sample 230 near the heater. The second thermocouple probe may be welded at the junction made with fine wires with a diameter of about 0.003 inches. Having a small thermal mass, the second thermocouple probe has minimal cold finger effect, and thus the temperature gradient a created between the two thermocouple probes by the thermal mass of the first thermocouple probe.

Figure 2C:
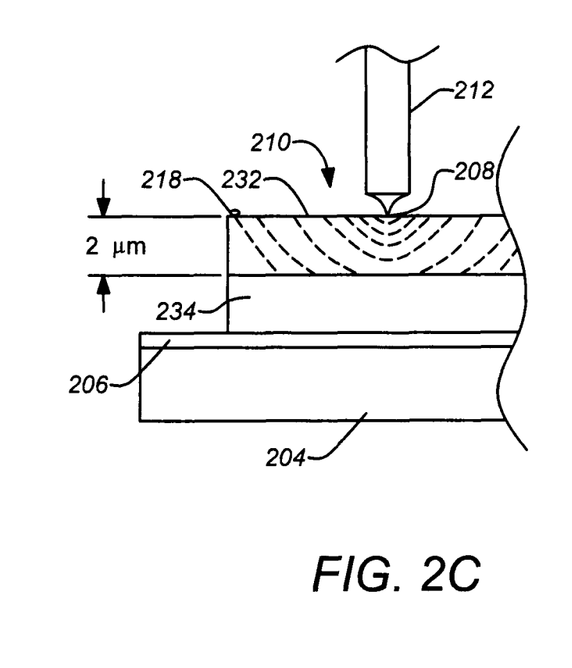
FIG. 2C is a schematic diagram of the exemplary apparatus for scanning measurement of the Seebeck coefficient at a local contact point of a sample for a thin film sample.

FIG. 2C is a close-up schematic diagram of the exemplary apparatus for scanning measurement of the Seebeck coefficient at a local contact point of a sample for a thin film sample. A typical thin film sample 232 may have a thickness of 2 μm or less. In addition, the thin film sample 232 may be supported on a substrate material 234 (e.g. silicon). As previously mentioned, one advantage of this measurement system 200 is that, the homogeneity of a film sample deposited on an original substrate 234 can be directly evaluated. This makes many of the typical sample preparation requirements unnecessary before measuring Seebeck coefficient of a thin film, and eliminates the chance of the materials degradation during any further processing steps that may normally be required for Seebeck measurements. For thin films, the second thermocouple probe 218 junction may located onto the front surface where the scanning first thermocouple probe 212 contacts the front surface 210 of the sample 232.

Both thermocouples may be constructed from copper and constantan wires (T-type) with the copper wire employed as a lead for the voltage reading. It is noted that, the thermocouple wires for the scanning probe may have the "cross" geometry, where wires threaded down a four-bore alumina tube are made to cross eachother at the end. In order to enable smooth linear motion of the thermocouple probe, the alumina thermocouple tube may be embedded into a hollow steel shaft, which is disposed through a linear sleeve bearing. A compressive spring may be attached onto the shaft end to allow the probe tip to press against the sample surface with a uniform, predefined force at each contact during measurement. The heater may be controlled with an Omega temperature controller, and kept at a substantially constant steady-state temperature to keep the ΔT between the thermocouple probes more than 10 degrees for both bulk and thin film samples. All measurements may be performed in a room temperature, ambient environment.

In one example, the LabVIEW program (functioning as both motorized stage control unit 226 and measurement unit 224) may be used for controlling movement of the xyz motorized stage 214, as well as measurement and recording of the data. For the xyz motorized stage 214, a compact 1 inch linear motorized translation stage (MTS25-Z8, Thorlabs Inc.) may used for all movement directions (axes). For the z direction, two alternate methods may be used to control the position during the measurement. In one method, the program learns the z-position of the surface prior to the scan, and the z-position of the probe is located an additional Δz of approximately 0.5 mm below the z-position of the surface to applie a repeatable contact force at the contact point. (Note: a much smaller Δz value may be employed for thin films.) below the surface when it makes measurement. In another method, the voltage reading of the first thermocouple probe may be monitored as the tip is lowered to the front surface of the sample. An open circuit measurement (when the tip is not making the contact), is indicatd because the voltage reading may be pinned up to large number showing a high voltage value. When the probe makes an electrical contact with the surface, the magnitude of the voltage is reduced to a few mV range. In one example, three channels in aKeithley 740 Scanning voltage meter may be assigned to register two thermocouple readings and one voltage reading. To prevent the thermal drift, the delta method is used for the measurement.

To establish the mechanical strength of the setup, the thermocouple probe head may be supported by a cage system with other components typically arranged in an optical bench setup. The rigidity and stability of the thermocouple probe head support may be provided by two poles which prevents the thermocouple probe head from shaking vertically (z-direction) during measurements. Details of exemplary thermocouple probes suitable for use in the present invention are described in the following section.

4. Exemplary Thermocouple Probe Design

Here, some features on the thermocouple design incorporated to improve temperature and voltage measurements are addressed. In a typical temperature measurement in high temperature environment, thermocouple types such as S or R, ones that contain platinum wires may be used. In one example setup, however, a thermocouple type which sustains up to approximately 925° K may be used, simply constructed from niobium and chromel wires. There are at least a couple of reasons for this selection.

First, as previously mentioned, a chemical reaction between the thermocouple and the sample may occur at their contact point and adversely affect the Seebeck slope and voltage offset. In order to minimize this effect, thermocouples having minimal reactivity with the sample should be chosen. Platinum thermocouples, while resistant to oxidation, are rather reactive to heavy metals such as Pb, Te, Ag, Bi and Sb. Even nickel has some reactivity with certain thermoelectric elements at high temperatures. Therefore, thermocouple wires that are inert to heavy metals may be preferable.

Another consideration in the selection of a thermocouple type due to the fact that Seebeck coefficient measurement systems typically use one of the thermocouple wires for the voltage measurement. It is noted that the Seebeck effect also occurs in the thermocouple wires, and the voltage reading is a summation of the Seebeck voltages from two wires in addition to the Seebeck voltage from the sample. Although voltages from the wires are opposite in polarity, they do not cancel each other because the magnitudes are not the same: the temperature differences between the contact points and the cold junction of the instruments are different. This residual voltage can falsely increase or decrease the measured Seebeck voltage, depending on the material charge carrier type.

The error induced by this factor is very apparent when measuring low Seebeck coefficient materials with high thermal conductivity (e.g. tungsten). To reduce this effect, a near-zero Seebeck coefficient metal, such as copper or niobium should be used for the voltage probe. This probe is also used as one leg of the thermocouple when combined with a high Seebeck coefficient metal. While the resulting thermocouple supplies only half the voltage of traditional thermocouples, measurement of this reduced signal is well within the capabilities of modern electronics.

For high temperatures, tungsten and niobium have been found to be preferable due to their low reactivity. In one example setup, a combination of niobium and chromium may be used. However, some minor drawbacks may be that these materials must be used in an oxygen free environment and are poor thermocouples for near-room temperature operation. However, embodiments of the invention may be implemented in vacuum or inert atmospheric environments (e.g. Argon, Helium, or Nitrogen). An oxygen environment may be used with proper selection of thermocouple materials (e.g. platinum). Other combinations of thermocouples include niobium/tungsten (up to 1000° C.), niobium/tungsten-rhenium, copper/constantan (type T, up to 350° C.), and gold-iron/chromel.

In order to provide an additional barrier against possible chemical reaction, a thin, flexible, graphite sheet (e.g. Grafoil from GrafTech International Inc, Ohio) may be used between the interface of the sample and thermocouple. With high thermal conductivity (approximately 5 W/mK at room temperature) and low electrical resistivity (approximately 1.15 mΩ·m at room temperature), these sheets also provide good thermal contact between the sample and the heating blocks while not interfering with the voltage measurements.

Figure 3A:
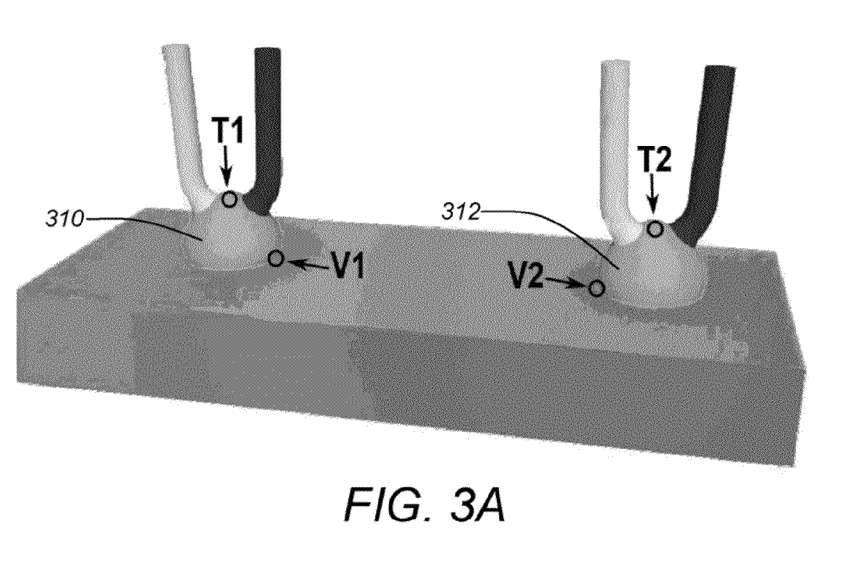
FIG. 3A shows an example of a Seebeck voltage and associated temperature measurement spatial dislocation.

FIG. 3A shows an example of a Seebeck voltage and associated temperature measurement spatial dislocation. This spatial variation can lead to errors when thermal gradients are present across the thermocouple beads 310, 312, the welded joints of the thermocouple. As shown, measured temperatures, T1 and T2, may be located at the tops of the thermocouple beads 310, 312, whereas the measured voltages, V1 and V2, are located at the base of the beads 310, 312 (at different temperatures). While many instruments measuring Seebeck coefficient utilize thermocouples with welded beads as shown in FIG. 3A, novel "crossed-wire" thermocouples described below offer definite advantages.

Figure 3B:
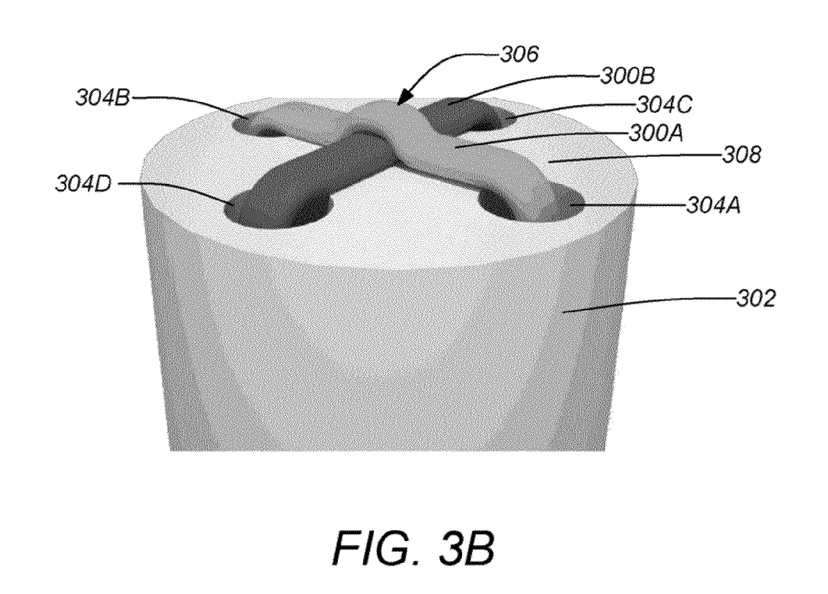
FIG. 3B shows an exemplary crossed-wire geometry may be applied to minimize Seebeck voltage and associated temperature measurement spatial dislocation.

FIG. 3B shows an exemplary crossed-wire geometry may be applied to minimize Seebeck voltage and associated temperature measurement spatial dislocation. In one example crossed geometry, two wires 300A, 300B (e.g. one niobium and one chromel) are made to cross threaded down a four-bore ceramic cylinder 302. Each wire 300A (or 300B) is threaded up one bore 304A (or 304C) and across the end surface 308 and back down an opposing bore 304B (or 304D). Here, the contact between the wires 300A, 300B is mechanical only (not welded) and governed only by the geometry of the crossed wires 300A, 300B. To minimize the temperature gradients across the thermocouple junction region, extremely thin (e.g. 0.1 mm diameter) wires 300A, 300B may be used. In contrast, thermocouple beads (e.g. in FIG. 3A) are typically approximately 1 mm in diameter. To further ensure that the junction is nearly isothermal, the ceramic cylinder 302 used to house the wires may be made of low thermal conductivity alumina (e.g. approximately 1.7 mm diameter). Note that an alternate ceramic material for the cylinder may be mullite. Although such a thin alumina cylinder may be delicate, the force loading is strictly compressive and along the length of the cylinder 302. The example cross-wire geometry may be employed with the measurement devices described herein where the cross-wire contacts are disposed at the end surface of the thermocouples probes in contact with the samples. One wire 300A lies directly over the other wire 300B at their contact point 306. In forming the two-wire thermocouple, the wire 300A material having the lower Seebeck coefficient of the two materials is disposed on top of the wire 300B material having the higher Seebeck coefficient, so that the lower Seebeck coefficient wire makes contact with the sample to minimize measurement error. This top wire 300A is also used to make the voltage measurement. (The top surface of the top wire 300A above the contact point 306 will be the contact point to the sample at the end of each thermocouple probe.) The crossed-wire design is additionally advantageous as it avoids the alloying and embrittlement typically associated with welding beads. The ability to simply and rapidly develop new thermocouple wire material combinations is a final advantage delivered by this geometry.

5. Scanning Seebeck Coefficient of Bulk Samples

One example that showing the usefulness of a Seebeck coefficient scanning technique is presented by Chen et. al APL 87, 171903, 2005, which is incorporated by reference herein. The bulk sample employed was LAST ($AgPb_mSbTe_{m+2n}$), which is known to have easy in phase segregations during fabrication. The XRD and SEM analysis were performed on this sample and showed no indication of inhomogeneity within the sample. The sub-mm range phase segregations were revealed only after the Seebeck coefficient mapping was conducted. This is a good example of detecting inhomogeneity in sample, in which traditional materials science tools has failed to detect.

In one example employing the present invention, two bulk samples of the n-type doped PbTe sample have been prepared at a company ('production sample'), and in the lab ('Caltech sample') and tested using an exemplary measurement instrument. It is noted that, although their compositions are very similar, they were processed employing different methods.

Figure 4A:
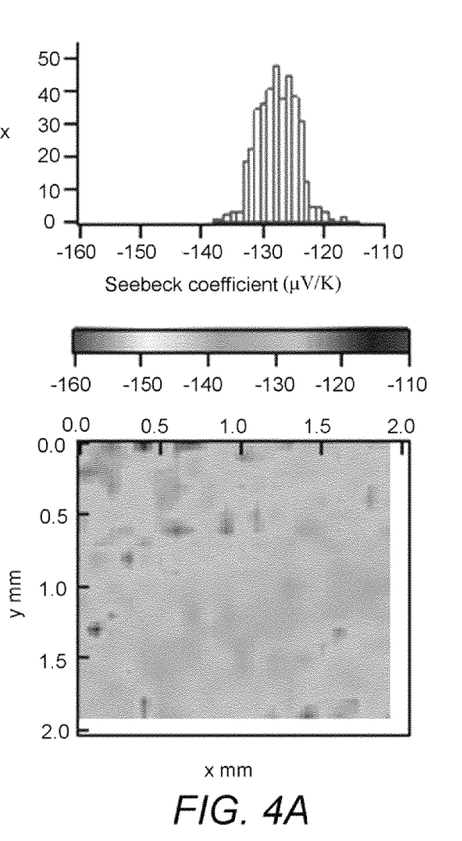
FIGS. 4A and 4B shows Seebeck coefficient scanning images and histograms of exemplary samples.
Figure 4B:
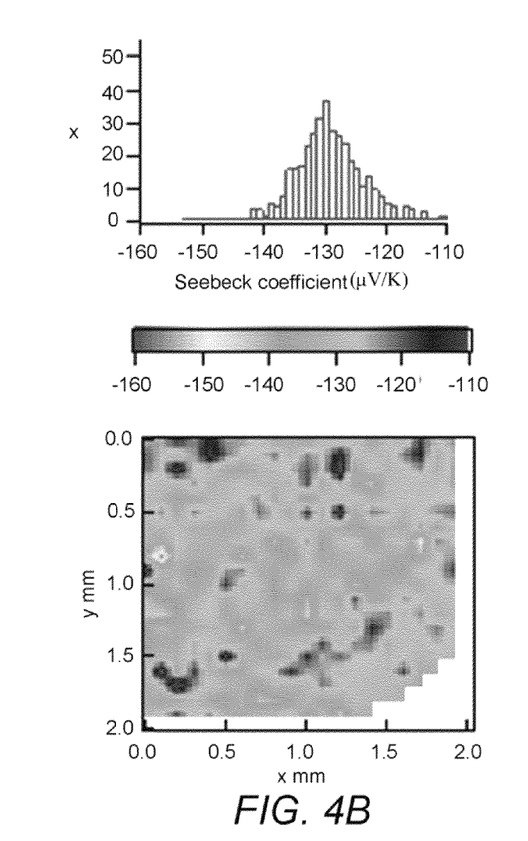

FIGS. 4A and 4B shows Seebeck coefficient scanning images and histograms of the exemplary samples. The scanned area is 2 mm×2 mm, with a data point interval of 100 μm. The average temperature of the samples is approximately 40 C and ΔT is approximately 15 C. The absolute value of the Seebeck coefficient is shown in various grades. As indicated in the histogram chart, the standard deviation of the Seebeck coefficient for the production sample is ±6.4 μV/K, while the Caltech sample is ±3.4 μV/K. These results reveal that although materials compositions are the same, the processing technique done at Caltech provides smaller local variations in the Seebeck coefficient.

Figure 5:
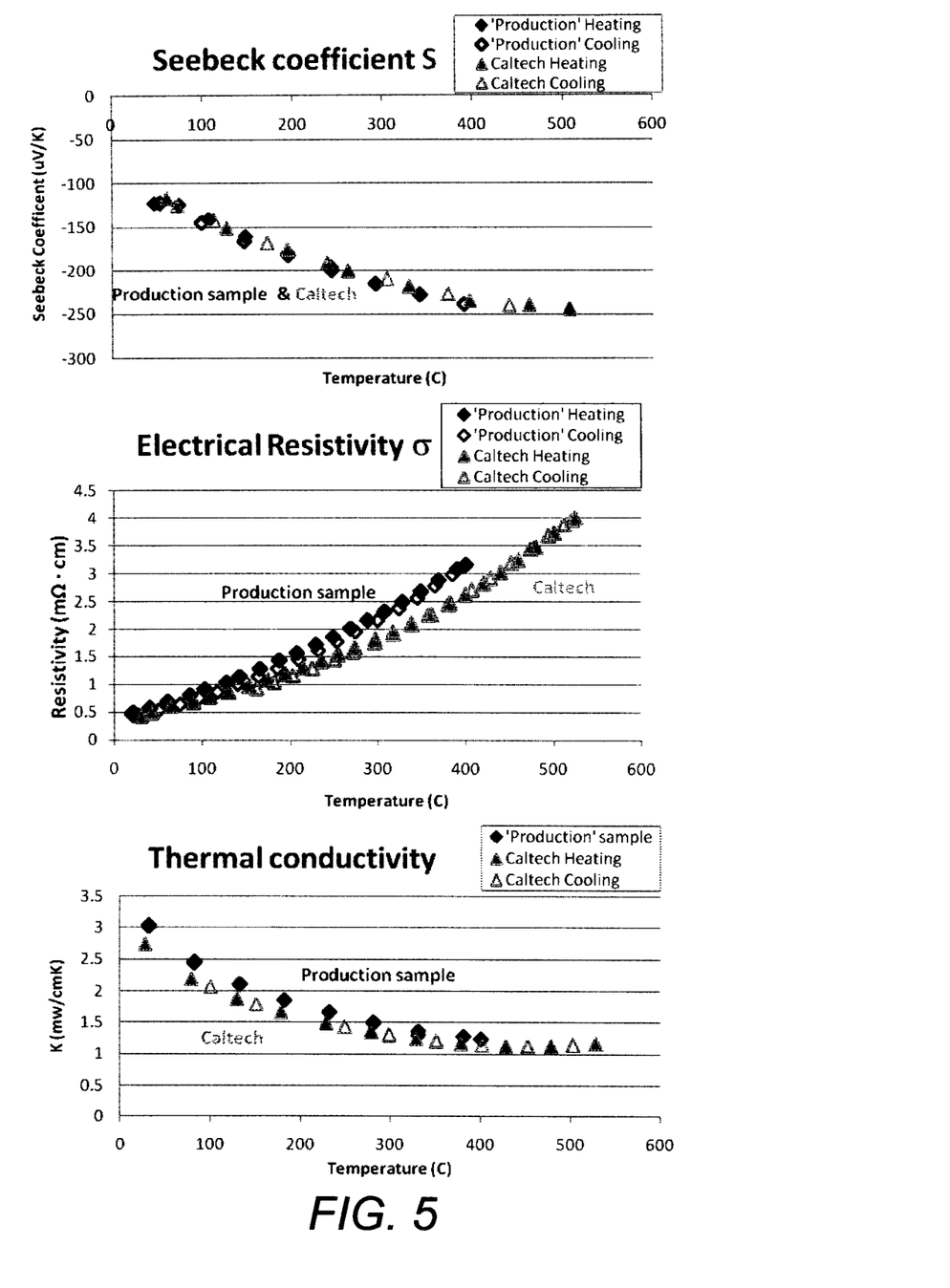
FIG. 5 shows graphs comparing the Seebeck coefficient, electrical resistivity and thermal conductivity of the two exemplary samples.

FIG. 5 shows graphs comparing the Seebeck coefficient, electrical resistivity and thermal conductivity of the two exemplary samples. It is noted that, for the purposes of this comparison only the Seebeck coefficient for these samples was measured at a single point, using a high temperature Seebeck coefficient measurement system, and not a scanning Seebeck coefficient measurement apparatus of the present invention. The electrical resistivity was evaluated by using the Van der Pauw method, and the thermal conductivity was evaluated by the thermal diffusivity data using the NETZSCH laser flash apparatus, and the heat capacity was estimated from the Blachnik equation. The results show that the Seebeck coefficients are similar for both samples for all temperature range measured, and the electrical resistivities and the thermal conductivities are slightly lower for the Caltech sample. These results indicate that, although thermoelectric properties are similar, homogeneity throughout the sample can be different depending on the how they are processed.

Figure 6A:
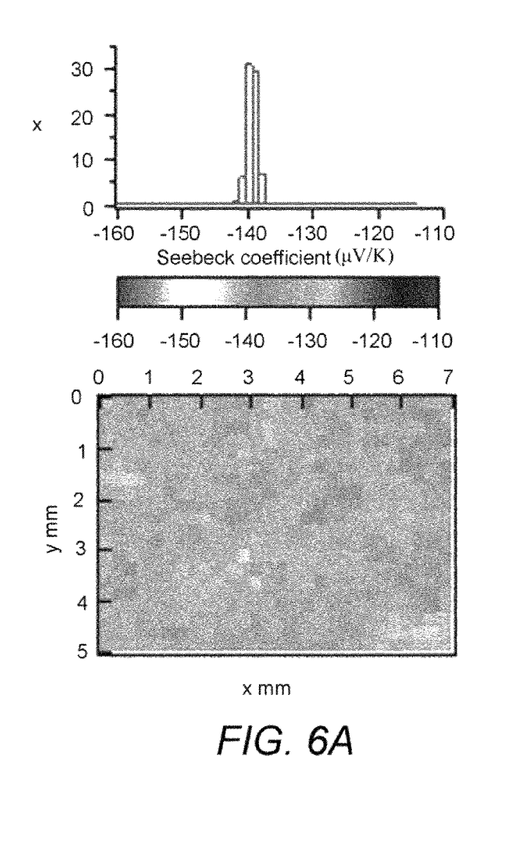
FIGS. 6A and 6B shows Seebeck coefficient scanning images and histograms of exemplary skutterudite samples.
Figure 6B:
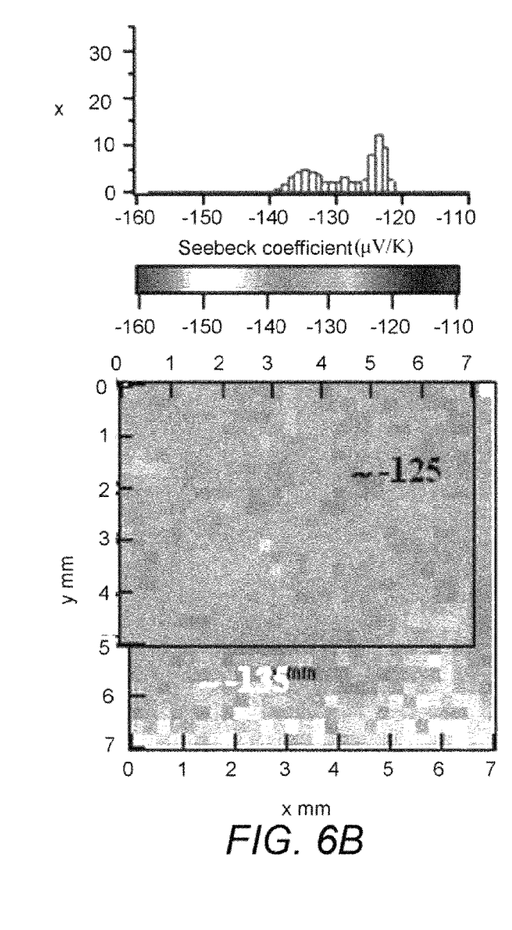

FIGS. 6A and 6B shows Seebeck coefficient scanning images and histograms of exemplary skutterudite samples which further illustrate the capability of the instrument. As before, each of the skutterudite were developed under a different process. The scanned image are shown for each sample, a 7 mm×5 mm image for Sample A of FIG. 6A and a 7 mm×7 mm image for Sample B of FIG. 6B, and their histograms. The sample point interval is 250 μm, with the average temperature of approximately 40 C, and ΔT of approximately 16 C. The scanned image for the Sample A has reveals the strikingly small standard deviation of 0.83 μV/K throughout the scanned region. The Sample B, on the other hand, shows greater variations in the absolute Seebeck coefficient value. The sample was re-scanned after rotating the sample for 90 degree, and its image was compared with the original scan. It has shown that both images reveal the same feature, indicating that the variation comes from intrinsic materials property, not from an instrument setup differences. It is noted that, the measurement to measurement variation of the Seebeck coefficient, evaluated by the standard deviation of 10 measurements on the same location, was 0.29 μV/K.

6. Scanning Seebeck Coefficient of Thin Film Samples

Figure 6C:
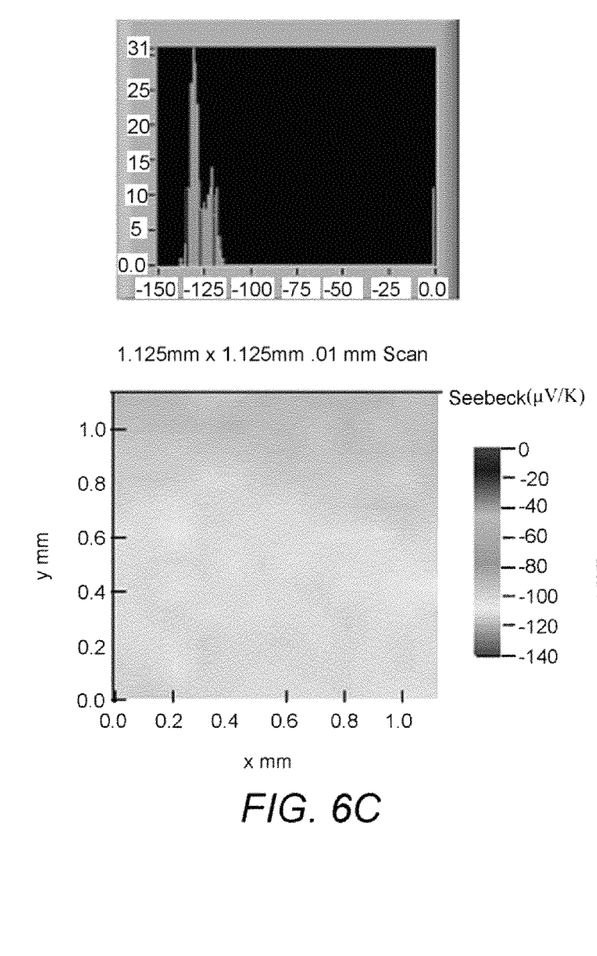
FIGS. 6C and 6D shows Seebeck coefficient scanning images and histograms of exemplary homogeneous and inhomogenous thin film samples, respectively.
Figure 6D:
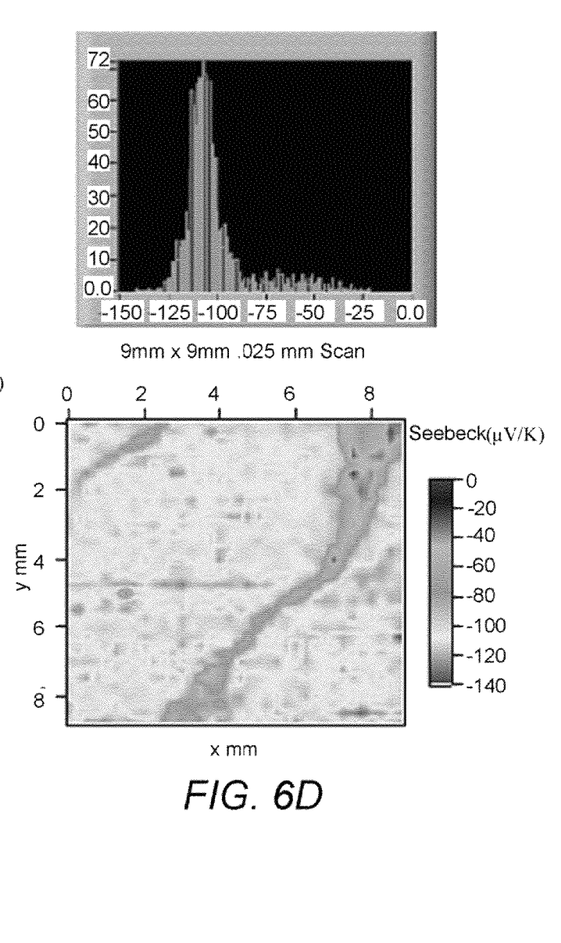

FIGS. 6C and 6D shows Seebeck coefficient scanning images and histograms of exemplary homogeneous and inhomogenous thin film samples, respectively. By setting up the instrument as in FIGS. 2A and 2C, the scanning Seebeck coefficient measurements may be demonstrated on the two thin film samples. FIG. 6C is a homogeneous thin film, whice FIG. 6D is an inhomogeneous thin film, each deposited on silicon wafer substrates. The thickness of films is approximately 3 to 5 μm. The scanned area is approximately 1.125× 1.125 $mm^2$ with the data point interval of approximately 100 μm for FIG. 6C, and the area of about 8×8 $mm^2$ with the data point interval of 250 μm for FIG. 6D. The instrument clearly revealed the variations of the materials segregation in a film sample in FIG. 6D, which appeared as the local variations in the Seebeck coefficient. It is noted that, the Seebeck coefficient measured using this technique reflects the in-plane characteristic. Although it may be a comparative measurement, this technique provides fast and less destructive way to find out homogeneity within a film sample. It is noted that the standard deviation of the Seebeck coefficient in FIG. 6C was about 1 to 2 μV/K.

Figure 7A:
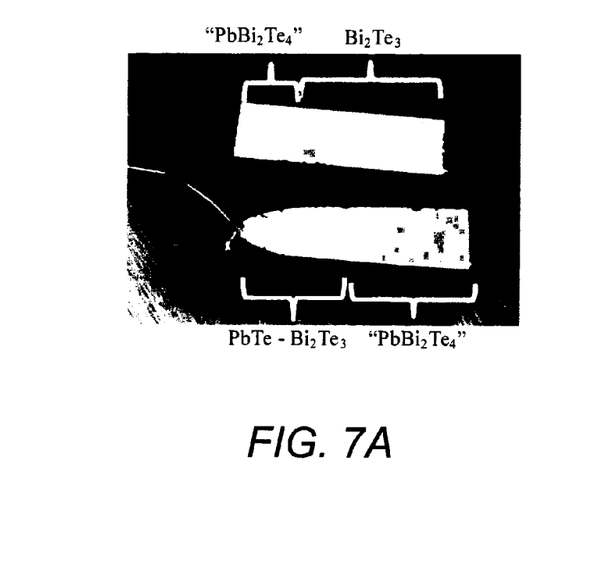
FIG. 7A shows a compositionally graded sample of $Pb_{14}Bi_{28.8}Te_{57.2}$.
Figure 7B:
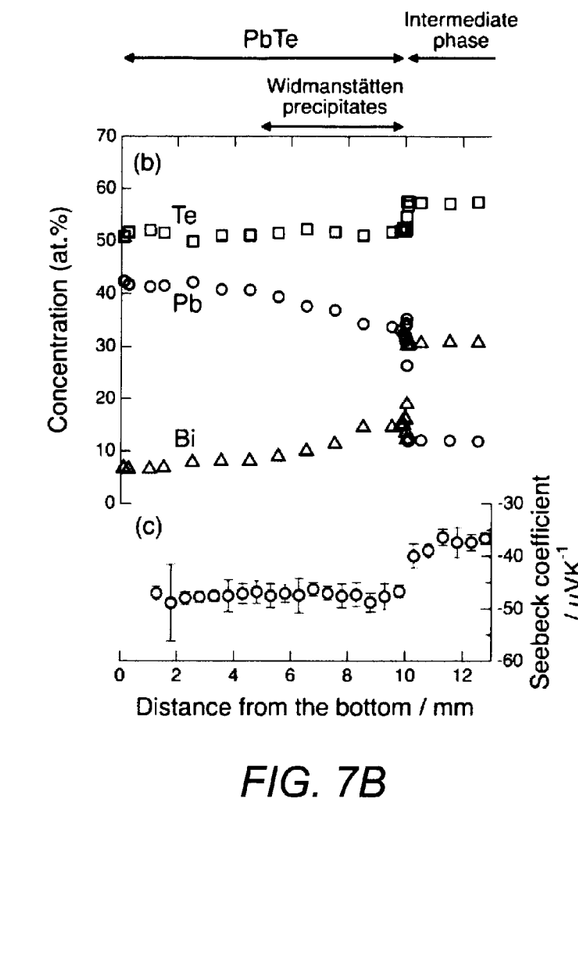
FIG. 7B shows graphs of the changes in composition and measured Seebeck coefficient of the $Pb_{14}Bi_{28.8}Te_{57.2}$ sample.

The previous examples show that the instrument yields a significantly low noise level. With this advantage, the instrument may be used for measuring the Seebeck coefficient of a compositionally graded material, as shown in FIG. 7A. The sample is an alloy with overall composition of $Pb_{14}Bi_{28.8}Te_{57.2}$, which was created by unidirectional solidification using the Bridgman method. FIG. 7B shows graphs of the changes in composition and measured Seebeck coefficient of the $Pb_{14}Bi_{28.8}Te_{57.2}$ sample. The measured Seebeck coefficient varies with the measurement location. Since the sample was buried in insulating epoxy to protect it from breakage, there was no access to the bottom surface of the sample. Accordingly, the junction of the second thermocouple probe was placed on a corner of the front surface.

Indium-gallium liquid metal was used at the junction to ensure a good electrical contact. FIG. 7B shows that the absolute Seebeck coefficient has slight increase at the Te rich region. It is noted that, the absolute Seebeck coefficient was measured on one spot using a different Seebeck coefficient system (a non-scanning measurement apparatus) and the difference of the absolute value was less than 5%.

7. Exemplary Method of Scanning Measurement of Seebeck Coefficient

Figure 8:
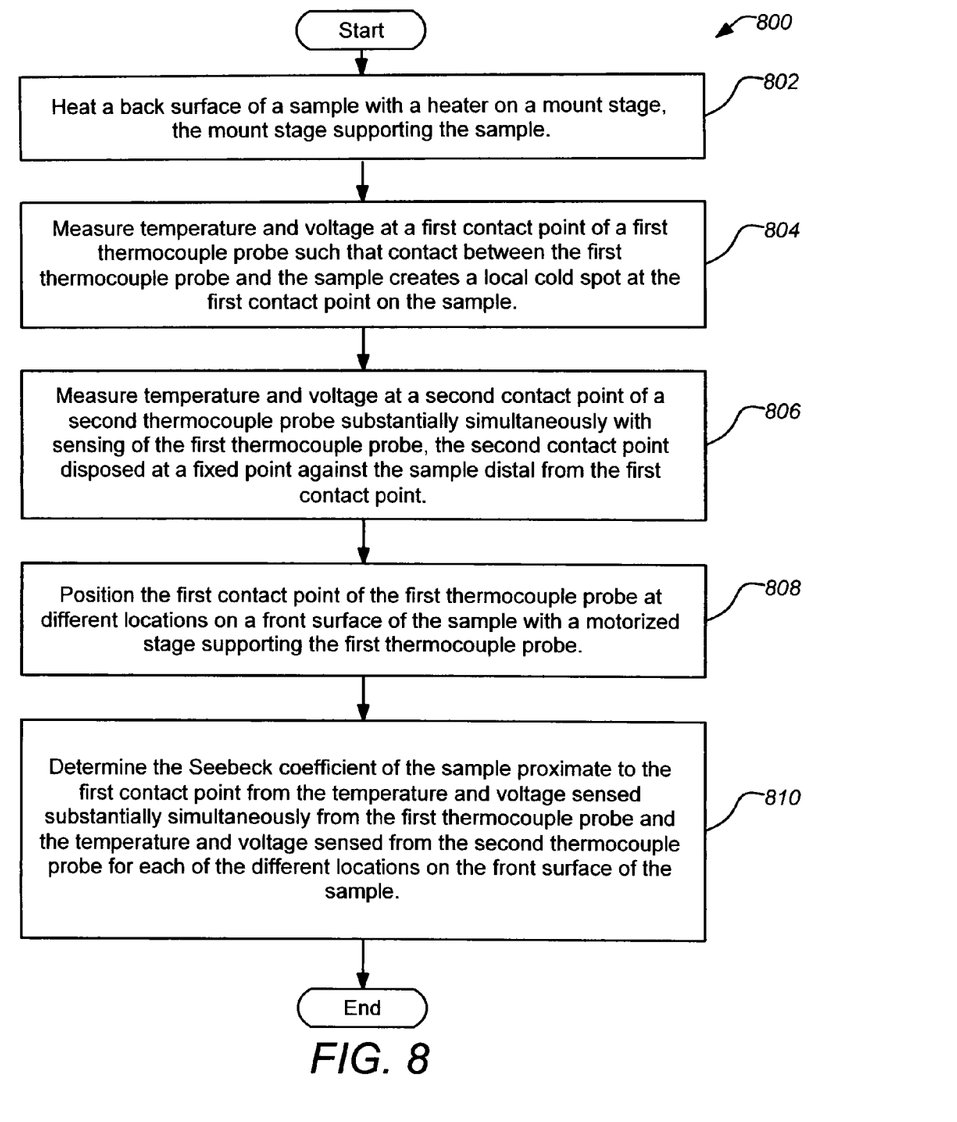
FIG. 8 is a flowchart of an exemplary method of scanning measurement of the Seebeck coefficient according to an embodiment of the invention.

FIG. 8 is a flowchart of an exemplary method 600 of measuring the Seebeck coefficient of a sample. The method 600 includes an operation 802 of heating a back side of the sample with a heater on a mount stage, the mount stage supporting the sample. In operation 804, temperature and voltage at a first contact point of a first thermocouple probe are measured such that contact between the first thermocouple probe and the sample creates a local cold spot at the first contact point on the sample. In operation 806, temperature and voltage at a second contact point of a second thermocouple probe are measured substantially simultaneously with sensing of the first thermocouple probe, the second contact point being disposed at a fixed point against the sample distal from the first contact point. In operation 808, the first contact point of the first thermocouple is positioned at different locations on a front surface of the sample with a motorized stage supporting the first thermocouple. Finally in operation 810, the Seebeck coefficient of the sample proximate to the first contact point is determined from the temperature and voltage measured substantially simultaneously from the first thermocouple probe and the temperature and voltage measured from the second thermocouple probe for each of the different locations on the front surface of the sample.

This method 800 may be altered consistent with the various apparatus embodiments previously described. It is important to note that the steps may be performed in any suitable order. In addition, although simultaneous measurement of temperature and voltage is ideal, it is not required and timing of the measurements may be manipulated to improve results as discussed hereafter.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. An apparatus for measuring a Seebeck coefficient of a sample, comprising:
   a mount stage for the sample, the mount stage having a heater for heating a back surface of the sample;
   a first un-heated thermocouple probe having a first contact point where temperature and voltage are measured;
   a second thermocouple probe having a second contact point where temperature and voltage are measured, the second contact point disposed at a fixed point against the sample distal from the first contact point; and
   a motorized stage supporting the first thermocouple probe for positioning the first contact point of the first thermocouple probe at different locations on a front surface of the sample;
   wherein contact between the first thermocouple probe and the sample creates a local cold spot at the first contact point on the sample and the Seebeck coefficient of the sample proximate to the second thermocouple probe for each of the different locations on the front surface of the sample.

2. The apparatus of claim 1, wherein the sample is a bulk sample and the second contact point is disposed on the back surface of the sample heated by the heater.

3. The apparatus of claim 1, wherein the sample is a thin film sample and the second contact point is disposed on the front surface of the sample near an edge of the sample.

4. The apparatus of claim 1, wherein the first thermocouple probe is spring loaded against the front surface of the sample at the first contact point to allow smooth consistent contact as the first thermocouple probe positioned to the different locations on the front surface of the sample.

5. The apparatus of claim 1, wherein the heater is operated to maintain the sample at a substantially steady state temperature.

6. The apparatus of claim 1, wherein a Seebeck coefficient image of the sample is generated from the Seebeck coefficient for each of the different locations on the front surface of the sample.

7. The apparatus of claim 1, wherein the first thermocouple probe comprises an electrically insulating cylinder having four bores exiting at an end surface of the cylinder and two thin wires, each wire threaded through two of the four bores and crossing to contact each other at the end surface.

8. The apparatus of claim 7, wherein the two thin wires comprise material combinations X/Y of niobium/chromel, niobium/tungsten, niobium/tungsten-rhenium, copper/constantan, or gold-iron/chromel, where X is a first wire material disposed on top of a second wire material Y.

9. The apparatus of claim 7, wherein the electrically insulating cylinder comprises a ceramic.

10. The apparatus of claim 9, wherein the ceramic comprises alumina.

11. method of measuring a Seebeck coefficient of a sample, comprising:
    heating a back surface of the sample with a heater on a mount stage, the mount stage supporting the sample;
    measuring temperature and voltage at a first contact point of a first un-heated thermocouple probe such that contact between the first thermocouple probe and the sample creates a local cold spot at the first contact point on the sample;
    measuring temperature and voltage at a second contact point of a second thermocouple probe substantially simultaneously with measuring of the first thermocouple probe, the second contact point disposed at a fixed point against the sample distal from the first contact point;
    positioning the first contact point of the first thermocouple probe at different locations on a front surface of the sample with a motorized stage supporting the first thermocouple probe; and
    determining the Seebeck coefficient of the sample proximate to the first contact point from probe and the temperature and voltage measured from the second thermocouple probe for each of the different locations on the front surface of the sample.

12. The method of claim 11, wherein the sample is a bulk sample and the second contact point is disposed on the back surface of the sample heated by the heater.

13. The method of claim 11, wherein the sample is a thin film sample and the second contact point is disposed on the front surface of the sample near an edge of the sample.

14. The method of claim 11, wherein the first thermocouple probe is spring loaded against the front surface of the sample at the first contact point to allow smooth consistent contact as the first thermocouple probe positioned to the different locations on the front surface of the sample.

15. The method of claim 11, wherein the heater is operated to maintain the sample at a substantially steady state temperature.

16. The method of claim 11, wherein a Seebeck coefficient image of the sample is generated from the Seebeck coefficient for each of the different locations on the front surface of the sample.

17. The method of claim 11, wherein the first thermocouple probe comprises an electrically insulating cylinder having four bores exiting at an end surface of the cylinder and two thin wires, each wire threaded through two of the four bores and crossing to contact each other at the end surface.

18. The method of claim 17, wherein the two thin wires comprise material combinations X/Y of niobium/chromel, niobium/tungsten, niobium/tungsten-rhenium, copper/constantan, or gold-iron/chromel, where X is a first wire material disposed on top of a second wire material Y.

19. The method of claim 17, wherein the electrically insulating cylinder comprises a ceramic.

20. The method of claim 19, wherein the ceramic comprises alumina.

21. An apparatus for measuring a Seebeck coefficient of a sample, comprising:
- a mount stage means for supporting the sample heating a back surface of the sample;
- a first un-heated thermocouple probe means for measuring temperature and voltage at a first contact point;
- a second thermocouple probe means for measuring temperature and voltage at a second contact point, the second contact point disposed at a fixed point against the sample distal from the first contact point; and
- a motorized stage means for supporting the first thermocouple probe means and for positioning the first contact point of the first thermocouple probe means at different locations on a front surface of the sample;
- wherein contact between the first thermocouple probe means and the sample creates a local cold spot at the first contact point on the sample and the Seebeck coefficient of the sample proximate to the first contact point is determined from the temperature and voltage measured from the first thermocouple probe means and the temperature and voltage measured from the second thermocouple probe means for each of the different locations on the front surface of the sample.

* * * * *